United States Patent [19]

Miyano

[11] 3,980,700

[45] Sept. 14, 1976

[54] PROSTAGLANDIN INTERMEDIATES AND OPTICALLY ACTIVE ISOMERS THEREOF

[75] Inventor: Masateru Miyano, Morton Grove, Ill.

[73] Assignee: G. D. Searle & Co., Chicago, Ill.

[22] Filed: Mar. 24, 1975

[21] Appl. No.: 561,647

Related U.S. Application Data

[60] Division of Ser. No. 187,508, Oct. 7, 1971, Pat. No. 3,888,905, which is a continuation-in-part of Ser. No. 799,965, Feb. 17, 1969, abandoned.

[52] U.S. Cl. .................. 260/520 B; 260/471 A; 260/473 A; 260/521 R
[51] Int. Cl.² ........................................ C07C 65/14
[58] Field of Search ........ 260/473 A, 520 B, 521 R, 260/471 A

[56] References Cited
OTHER PUBLICATIONS

Miyano, M. et al., Tetrahedron Letters No. 20, pp. 1615–1618, 1969.

*Primary Examiner*—Paul J. Killos
*Attorney, Agent, or Firm*—John A. Dhuey

[57] ABSTRACT

The condensation of dimethyl 3-oxoundecane-1,11-dioate with styrylglyoxal affords 14-phenyl-9,12-dioxo-11-hydroxytetradec-13-enoic acid, which is cyclized to afford 3-hydroxy-5-oxo-2-styrylcyclopent-1-eneheptanoic acid. Hydroxylation of the styryl double bond affords the corresponding 2-($\alpha,\beta$-dihydroxyphenethyl) derivative. Resolution of the racemic 2-styryl-3-hydroxy compounds with either (−) or (+)-O-methylmandelyl chloride yields the optically active isomers which are separated chromatographically. The instant compounds are useful as anti-microbial, anti-fungal and hypotensive agents, as prostaglandin ($PGE_2$) antagonists and also as intermediates to prostanoic acid derivatives and their optically active isomers which exhibit anti-microbial, pepsin-inhibitory, hypotensive and smooth muscle-contracting properties.

6 Claims, No Drawings

PROSTAGLANDIN INTERMEDIATES AND OPTICALLY ACTIVE ISOMERS THEREOF

This application is a division of my copending application Ser. No. 187,508, filed Oct. 7, 1971 now U.S. Pat. No. 3,888,905, which is a continuation-in-part of my application Ser. No. 799,965, filed Feb. 17, 1969, now abandoned.

The present invention is concerned with novel chemical compounds characterized by a 2-substituted cyclopentane structure and, more particularly, with compounds of the following structural formula

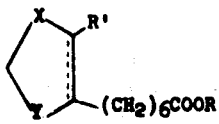

wherein the dashed line indicates the optional 1,2 double bond, R can be hydrogen or a lower alkyl radical, R' is a styryl, phenethyl or α,β-dihydroxy radical, X is a carbonyl or methylene radical or a radical of the formula

with Z being hydroxy, (−)-menthoxyacetoxy, (−) or (+)-0-methylmandeloxy, (lower alkanoyl)oxy or chloro(lower alkanoyl)oxy and the wavy lines represent the α or β stereochemical configurations or the racemic mixture and Y is a methylene, hydroxyiminomethylene, semicarbazonomethylene or carbonyl radical.

The lower alkyl radicals represented by R are typified by methyl, ethyl, propyl, butyl, pentyl, hexyl, heptyl and the branched-chain groups isomeric therewith.

Illustrative of the lower alkanol radicals encompassed by the X term are formyl, acetyl, propionyl, butyryl, vareryl, caproyl, heptanoyl and the corresponding branched-chain isomers.

Starting materials suitable for the manufacture of the compounds of this invention are styrylglyoxal, conveniently prepared by the selenous acid oxidation of 4-phenyl-3-buten-2-one, and the dialkyl esters of 3-oxoundecane-1,11-dioic acid. Dimethyl 3-oxoundecane-1,11-dioate is thus saponified with potassium hydroxide and the resulting dicarboxylic acid is allowed to react with styrylglyoxal, thus affording 14-phenyl-9,12-dioxo-11-hydroxytetradec-13-enoic acid. Cyclization of the latter intermediate in the presence of potassium hydroxide results in the instant 3-hydroxy-5-oxo-2-styrylcyclopent-1-eneheptanoic acid.

The instant 2-(α,β-dihydroxyphenethyl) derivatives are readily obtained by hydroxylation of the corresponding 2-styryl compounds. A convenient reagent is osmium tetroxide. The instant methyl 3-acetoxy-5-oxo-2-styrylcyclopent-1-eneheptanoate is thus contacted at room temperature with osmium tetroxide in dioxane to produce methyl 3-acetoxy-5-oxo-2-(α,β-dihydroxyphenethyl)cyclopent-1-eneheptanoate.

A convenient procedure for manufacture of the 2-formyl compounds consists of cleaving the glycol structure of the corresponding 2-(α,β-dihydroxyphenethyl) substances. 3-Acetoxy-5-oxo-2-(α,β-dihydroxyphenethyl)cyclopent-1-eneheptanoate in ethanol is contacted with aqueous sodium periodate, thus affording 3-acetoxy-2-formyl-5-oxocyclopent-1-eneheptanoate. The 2-formyl compounds are alternatively produced from the corresponding 2-styryl derivatives by combining the hydroxylation and cleavage processes. Methyl 3-hydroxy-5-oxo-2-styrylcyclopent-1-eneheptanoate in aqueous dioxane is thus allowed to react with osmium tetroxide and sodium periodate to afford methyl 2-formyl-3-hydroxy-5-oxocyclopent-1-eneheptanoate.

Oxidation of the instant 3-hydroxy compounds results in the corresponding 3,5-dioxo substances. Chromium trioxide in pyridine thus converts methyl 3-hydroxy-5-oxo-2-styrylcyclopent-1-eneheptanoate to methyl 3,5-dioxo-2-styrylcyclopent-1-eneheptanoate.

Condensation of the 2-styryl-5-oxo compounds with an hydroxylamine yields the instant oxime derivatives. For example, treatment of 3-hydroxy-5-oxo-2-styrylcyclopent-1-eneheptanoic acid with hydroxylamine hydrochloride and sodium acetate in aqueous methanol yields 3-hydroxy-5-hydroxyimino-2-styrylcyclopent-1-eneheptanoic acid. In a similar manner, condensation of the 2-styryl-5-oxo compounds with a semicarbazide yields the 2-styryl-5-semicarbazono derivatives of this invention. Typically, 3-hydroxy-5-oxo-2-styrylcyclopent-1-eneheptanoic acid is allowed to react with semicarbazide hydrochloride, thus affording 3-hydroxy-5-semicarbazono-2-styrylcyclopent-1-eneheptanoic acid.

The 5-desoxo compounds may be produced by contacting the 5-oxo-2-styryl derivatives with a reducing agent such as sodium borohydride. In that manner 3-oxo-2-styrylcyclopent-1-eneheptanoic acid is produced from the sodium borohydride reduction of 3-hydroxy-5-oxo-2-styrylcyclopent-1-eneheptanoic acid.

The 2-phenethyl derivatives are conveniently prepared by hydrogenating the 2-styryl substances with hydrogen in the presence of palladium-on-carbon catalyst and separating the products chromatographically. Thus, when 3-hydroxy-5-oxo-2-styrylcyclopent-1-eneheptanoic acid is allowed to react with hydrogen in the presence of 5% palladium-on-carbon catalyst, there is produced, after separation by chromatography on silicic acid, 2β-phenethyl-5-oxo-1α-cyclopentaneheptanoic acid, 2β-phenethyl-5-oxo-1α-cyclopent-3-eneheptanoic acid, 2-phenethyl-5-oxocyclopent-1-eneheptanoic acid, 3β-hydroxy2β-phenethyl-5-oxo-1α-cyclopentaneheptanoic acid, 3-hydroxy-2-phenethyl-5-oxocyclopentaneheptanoic acid, 3α-hydroxy-2β-phenethyl-5-oxo-1α-cyclopentaneheptanoic acid and 3-hydroxy-2-phenethyl-5-oxocyclopent-1-eneheptanoic acid.

The optically active 2-styryl substances of this invention can be manufactured by resolving the racemic 3-hydroxy-2-styryl compounds with (−)-0-methylmandelyl chloride to produce the 3α(−)-0-methylmandeloxy and 3β-(−)-0-methylmandeloxy derivatives. The latter compounds are conveniently fractionated on silicic acid to yield the separated 3α and 3β isomers. Subsequent reaction of the latter compounds with base, such as potassium carbonate, affords the 3α-hydroxy and 3β-hydroxy 2-styryl compounds. Those optically active derivatives may then be processed in the same manner as the racemic mixtures to yield optically active prostaglandins. For example, the 3β and 3α-hydroxy-2-styryl compounds may be hydroxylated and cleaved to yield the 3β and 3α-hydroxy-2-formyl compounds, respectively. Those compounds are then allowed to react with hexanoylmethylene triphenyl phosphorane to produce respectively, the 11β and 11α-hydroxy prostanoic acid derivatives.

As an example of the preceding manufacturing sequence, 3-hydroxy-5-oxo-2-styrylcyclopent-1-eneheptanoic acid is treated with (−)-0-methylmandelyl chloride to yield, after chromatography on silicic acid, separated fractions of 3β-((−)-0-methylmandeloxy)-5-oxo-2-styrylcyclopent-1-eneheptanoic acid and 3α-((−)-0-methylmandeloxy)-5-oxo-2-styrylcyclopent-1-eneheptanoic acid. The latter compound is treated with aqueous potassium carbonate to yield a product, which when chromatographed on silicic acid, affords (−)-3α-hydroxy-5-oxo-2-styrylcyclopent-1-eneheptanoic acid. Hydroxylation of that compound with osmium tetroxide followed by cleavage with sodium periodate affords (−)-2-formyl-3α-hydroxy-5-oxocyclopent-1-eneheptanoic acid. Treatment of the 3β-derivative, in a similar manner, affords (+)-2-formyl-3β-hydroxy-5-oxocyclopent-1-eneheptanoic acid.

The compounds of this invention exhibit valuable pharmacological properties. They are anti-microbial agents as is evidenced by their anti-bacterial properties, in particular against *Erwinia sp.* and *Diplococcus pneumoniae*, and their anti-protozoal activity, e.g. against *Trichomonas vaginalis* and *Tetrahymena pyriformis*. In addition, they are hypotensive agents and prostaglandin ($PGE_2$), bradykinin, acetylcholine and seerotonin antagonists.

The anti-bacterial property of the instant compounds is specifically illustrated by the activity of 3-hydroxy-5-oxo-2-styrylcyclopent-1-eneheptanoic acid, methyl 3-acetoxy-2-(α,β-dihydroxyphenethyl)-5-oxocyclopent-1-eneheptanoate and methyl 2-(α,β-dihydroxyphenethyl-)-3,5-dioxocyclopent-1-eneheptanoate when tested in the following assay:

Sterile blood agar is inoculated with a 24 hour broth culture of the bacterium, *Diplococcus pneumoniae*, whereupon approximately 5 mg. of the test compound is placed on the inoculated agar surface. The agar is then incubated at 37° C. for 24 hours, at the end of which time it is observed for zones of inhibition in the area immediately surrounding the test compound. Compounds which are effective in causing a zone of inhibition are designated active.

The antibacterial utility of the instant compounds further is evident from the results of standardized tests whereby nutrient broth (manufactured by Baltimore Biological Laboratories or Difco) is prepared at twice the concentration recommended by the manufacturer, sterilized, and inoculated with 2% (by volume) of a culture of *Erwinia sp*. Meanwhile, compound is heated in sterile distilled water at a concentration of 2000 γ per ml. and a temperature of 80° C. for 20 min. An equivolume mixture of this compound preparation and the inoculated broth is incubated aerobically at 37° C. and then examined grossly for the growth of the test organism. The incubation period is 24–48 hr. If growth of the test organism is observed, the compound is considered inactive. If no such growth is observed, the incubated mixture is serially diluted and mixed with an inoculated broth of the same composition as before excepting that the concentration is halved and 1% (by volume) of the culture instead of 2% is incorporated. Amounts of the latter broth added are such that concentrations of 100, 10, and 1 γ of compound per ml. result. The mixtures thus obtained are incubated as before and then examined grossly for growth of the test organism. Potency is expressed as the minimum concentration at which no growth of test organism is discernible. Controls are provided by concurrent incubations identical with the foregoing except for the absence of compound.

The anti-protozoal property of the instant compounds is evidenced by the activity of methyl 3,5-dioxo-2-styrylcyclopent-1-eneheptanoate, 3-hydroxy-5-oxo-2-styrylcyclopent-1-eneheptanoic acid and methyl 3-acetoxy-2-(α,β-dihydroxyphenethyl)-5-oxocyclopent-1-eneheptanoate when assayed as follows:

To 80 volumes of modified Diamond medium prepared by mixing 1200 parts of trypticase (Baltimore Biological Laboratories), 600 parts of yeast extract (Difco), 300 parts of maltose, 60 parts of L-cysteine hydrochloride, 12 parts of L-ascorbic acid, 48 parts of dibasic potassium phosphate, 48 parts of monobasic potassium phosphate, and 54,000 parts of distilled water, adjusting the pH to 6.8 with 4% aqueous sodium hydroxide, incorporating 30 parts of agar (Baltimore Biological Laboratories), boiling for 1 minute to dissolve the agar, and sterilizing in an autoclave, is added aseptically 20 volumes of sterile Dubos medium serum. The resulting medium is inoculated with 1% by volume of a 72 hour culture of Trichomonas vaginalis, whereupon 1 ml. of the inoculated medium is mixed with 10 mg. of test compound. The mixture is incubated anaerobically at 37° C. for 48 hours, then is examined microscopically for the presence of motile trichomanads. If any are observed, the compound is considered inactive. If no motile trichomonads are observed, 0.1 ml. of the incubated mixture is serially diluted and mixed with additional quantities of the inoculated medium sufficient to produce concentrations of 1,000, 100, 10 and 1 mcg. of test compound per ml. and the resulting mixtures are inoculated anaerobically as before at 37° C. for 48 hours, then are examined microscopically for the presence of motile trichomonads. Controls are provided by concurrent incubations identical with the foregoing except for the absence of the test compound.

Further evidence for the anti-protozoal activity of the compounds of this invention is provided by the following assay, wherein 3-hydroxy-5-oxo-2-styrylcyclopent-1-eneheptanoic acid, for example, has been found active:

A solution is prepared from 24 g. of proteose peptone, 16 g. of sucrose and 1000 ml. of distilled water. 0.5 Ml. of this solution is inoculated with 10% by volume of a 4-7 day old culture of *Tetrahymena pyriformis* and the resulting mixture is added to 0.5 ml. of a solution or suspension containing 2 mg. of test compound per ml. of solution. The resulting mixture is incubated at room temperature for 48 hours, then examined microscopically for the presence of motile protozoa. If any are observed, the compound is considered inactive. If no motile protozoa are observed, 0.1 ml. of the incubated mixture is serially diluted and mixed with additional quantities of the inoculated medium sufficient to produce concentrations of 1,000, 100, 10 and 1 mcg. of the test compound per ml. and the resulting mixtures are incubated as before at room temperature for 48 hours, then are examined microscopically for the presence of motile protozoa. Controls are provided by concurrent incubations identical with the foregoing except for the absence of the test compound.

The hypotensive property of the instant compounds is exemplified by the activity of methyl 3,5-dioxo-2-styrylcyclopent-1-eneheptanoate and 3-hydroxy-5-oxo- 2-styrylcyclopent-1-eneheptanoic acid when tested as follows:

This assay is substantially that described by Pickens et al., Circ. Res., 17, 438 (1965). Male Charles River rats weighing 100–350 g. are used. Each animal is anesthetized by intraperitoneal injection of 50 mg./kg. of sodium pentylbarbital, whereupon cardiovascular reflexes are blocked by subcutaneous injection of 3 mg. of atropine sulfate dissolved in 0.3 ml. of aqueous 0.85% sodium chloride and sensitization is induced by subcutaneous injection of 5 mg. of pentolinium tartrate dissolved in 1 ml. of aqueous 0.85% sodium chloride. The trachea is intubated and both femoral veins and a femoral artery are cannulated, the latter being connected to a calibrated transducer, amplifier and recorder. After surgery, 5 mg./kg. of heparin sodium is introduced via one of the venous cannulae as a 2% solution in aqueous 0.85% sodium chloride and rectal temperature is adjusted to 32°C. by means of a regulator and external heat source. When the animal's blood pressure and temperature have stabilized, five consecutive 0.1 ml. doses of angiotensin spaced 3 minutes apart are administered via one of the venous cannulae, followed immediately by a dose of the test compound dissolved or suspended in water q.s. a concentration of 10 mg./ml. and administered via the other venous cannula. After 15 minutes, the angiotensin dosage is repeated, whereupon the mean response to the precompound treatment with angiotensin is determined and compared with the mean response to the post-compound angiotensin treatment. The compound is considered hypotensive if it significantly ($P \leq 0.05$) decreases the mean response to angiotensin in more than half of the test animals.

The antifungal utility of the instant compounds is evident from the results of standardized tests whereby two concentrations of Sabouraud dextrose agar (manufactured by Baltimore Biological Laboratories or Difco) are prepared, one as recommended by the manufacturer and the other at twice this concentration. These preparations are sterilized and then maintained in a fluid state at 80°C. Meanwhile, compound is heated in sterile distilled water at a concentration of 2000 γ per ml. and a temperature of 80°C. for 20 min. An equivolume mixture of this compound preparation and the double-strength agar is serially diluted and mixed with the single-strength agar in amounts such that concentrations of 1000, 100, 10, and 1 γ of test compound per ml. result. The mixtures thus obtained are allowed to cool and solidify, whereupon they are surface-inoculated with a suspension of *T. mentagrophytes*, *C. albicans*, *Fusarium sp.*, or *V. albo-atrum* and then incubated aerobically at room temperatures. The incubation period is 6–7 days for *T. mentagrophytes*, 48 hours for *C. albicans*, and 5–7 days for *Fusarium sp.* and *V. albo-atrum*. Activity is determined by gross examination and the potency is expressed as the minimum concentration at which no growth of the test organism is discernible. Controls are provided by concurrent incubations identical with the foregoing except for the absence of compound.

The prostaglandin, acetylcholine, bradykinin and 5-hydroxytryptamine antagonist activity is demonstrated in the following procedure which is substantially the same as that described by J. H. Sanner, *Arch. int. Pharmacodyn.*, 180 (1), 46 (1969):

Female albino guinea pigs weighing 200–500 g. are sacrificed by cervical dislocation and the ileum is quickly removed and placed in modified Tyrode solution containing one-half the usual amount of magnesium ions. Segments of ileum, about 2 centimeters long, are cut and mounted in a 2 or 4 ml. tissue bath containing the modified Tyrode solution. The solution is maintained at 37° and bubbled with a gaseous mixture of 95% oxygen and 5% carbon dioxide. Contractions are detected isotonically. Approximately equal submaximal contractions are obtained in preliminary trials by adjusting the doses of prostaglandin $F_2$ ($PGE_2$), 5-hydroxytryptamine, and acetylcholine added to the bath. Two control contractions are obtained at 3.5 minute intervals. A solution or suspension of the test compound in the bathing solution is then substituted for the original modified Tyrode solution. The test suspension is kept in constant contact with the tissue for the remainder of the experiment except for brief periods to drain the bath in preparation for rinsing with fresh test suspension. Three more contractions are elicited to each agonist in the presence of the test compound without interrupting the time sequence. The last two sets of treated responses are compared with the two sets of control responses. The first set of treated responses is not used for comparisons, being used only to maintain the timed sequence of injections during the period allowed for the tissue to become equilibrated with the antagonist. A compound is rated active if the mean of contractions produced by any agonist is reduced 75% or more by the test compound.

The instant compounds are useful also as intermediates in the manufacture of novel prostanoic acid derivatives and their optical isomers of the following structural formula

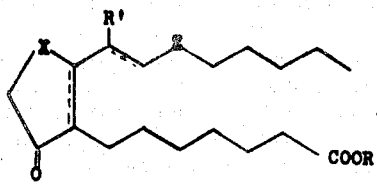

wherein R is hydrogen or a lower alkyl radical, as defined hereinbefore, R' is hydrogen or a hydroxy group, X is a hydroxymethylene or lower (alkanoyl)oxy methylene radical, Z is a carbonyl or hydroxymethylene group and the dotted line indicates an optional 8,12 and 13,14 double bond. The lower alkanoyl radicals are as defined hereinbefore.

A specific example of the manufacture of one of the latter compounds is the reaction of methyl 3-acetoxy-2-formyl-5-oxocyclopent-1-eneheptanoate with hexanoylmethylene triphenyl phosphorane to afford methyl 11-acetoxy-9,15-dioxo-prosta-8(12), 13-dienoate. These prostanoic acid derivatives display valuable pharmacological properties. They are thus hypotensive, smooth muscle-contracting, anti-bacterial, anti-protozoal, anti-fungal and pepsin-inhibitory agents.

The following examples describe in detail compounds illustrative of the present invention and methods which have been devised for their manufacture. The invention, however, is not to be construed as limited thereby either in spirit or in scope since it will be apparent to those skilled in the art that many modifications both of materials and of methods may be practiced without departing from the purpose and intent of this disclosure.

It is understood that the procedures applied to racemic mixtures are applicable to the optically active isomers as well. Throughout these examples temperatures are given in degrees Centigrade and relative amounts of materials in parts by weight except as otherwise noted.

EXAMPLE 1

A solution containing 100 parts of 4-phenyl-3-buten-2-one, 106 parts of selenous acid, 160 parts of dioxane and 20 parts of water is heated to the reflux temperature. After the initial vigorous reaction has subsided, the mixture is heated at that temperature for an additional 30 minutes. The supernatant is then decanted from the metallic selenium and is concentrated under reduced pressure. Distillation of the residue under reduced pressure affords, as a yellow oil, styrylglyoxal, boiling at about 120° at 2.5 mm. pressure.

EXAMPLE 2

A solution of 38.2 parts of dimethyl 3-oxoundecane-1,11-dioate in 200 parts by volume of 10% aqueous potassium hydroxide is stored at 0°–5° for about 3 days, then is adjusted to pH 5 by the addition of concentrated aqueous citric acid. To that mixture is added a solution which is prepared by heating 21.9 parts of styrylglyoxal in 50 parts by volume of 50% aqueous methanol at 65°–75° for about 20 minutes, then adding 60 parts of methanol. To the resulting reaction mixture is added 30 parts by volume of 1 M pH 4.5–5.0 citrate buffer and stirring at room temperature is continued for about 3 hours, during which time carbon dioxide gas is evolved. The precipitated product is collected by filtration, thus affording the half potassium salt of 14-phenyl-9,12-dioxo-11-hydroxytetradec-13-enoic acid, melting at about 105°. Further purification by recrystallization from methanol affords the pure compound, melting at about 107.5°.

The latter half potassium salt is dissolved in water and the resulting aqueous solution is acidified by the addition of dilute hydrochloric acid. The resulting acidic mixture is extracted with ether and the ether layer is separated, washed with water, dried over anhydrous sodium sulfate and concentrated to dryness. The resulting solid residue is purified by recrystallization from chloroform-ether to yield 14-phenyl-9,12-dioxo-11-hydroxytetradec-13-enoic acid, melting at about 81.5°–83°.

EXAMPLE 3

To 3000 parts by volume of an aqueous solution containing 6.7 parts of potassium hydroxide is added, with stirring at 21°–23° over a period of about 2¼ hours, a solution of 10.4 parts of 14-phenyl-9,12-dioxo-11-hydroxytetradec-13-enoic acid in 187 parts of chloroform. After completion of the addition, the reaction mixture is stirred for an additional 2 hours, then is made acidic by adding 10 parts of oxalic acid dihydrate. The acidic mixture is extracted with chloroform and the organic layer is washed with dilute aqueous sodium chloride, then dried over anhydrous sodium sulfate and concentrated to dryness under reduced pressure. The resulting residue is recrystallized first from benzene, then from chloroform-ether to yield 3-hydroxy-5-oxo-2-styrylcyclopent-1eneheptanoic acid, which displays a melting point at about 118°. This compound displays an ultraviolet absorption maximum at about 325 millimicrons with a molecular extinction coefficient of about 36,400 and is further characterized by the following structural formula

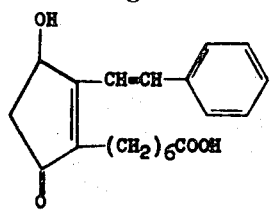

EXAMPLE 4

A mixture containing 44.3 parts of 3-hydroxy-5-oxo-2-styrylcyclopent-1-eneheptanoic acid, 11.3 parts of diazomethane and 700 parts of ether is kept at room temperature for about 5 minutes, at the end of which time acetic acid is added in order to destroy the excess reagent. The resulting mixture is then washed with aqueous sodium bicarbonate, dried over anhydrous sodium sulfate and stripped of solvent by distillation under reduced pressure. The residue is purified by chromatography, first on silica gel followed by elution with 50% ethyl acetate in benzene, then by dry chromatography on silica gel containing 8% water, also using 50% ethyl acetate in benzene, thus affording methyl 3-hydroxy-5-oxo-2-styrylcyclopent-1-eneheptanoate. This compound is characterized by infrared absorption maxima, in chloroform, at about 2.75, 2.87, 5.76, 5.88 and 6.17 microns and by an ultraviolet absorption maximum at about 325 millimicrons with a molecular extinction coefficient of about 36,000. It is represented by the following structural formula

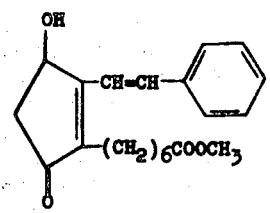

EXAMPLE 5

A solution containing 0.9 part of methyl 3-hydroxy-5-oxo-2-styrylcyclopent-1-eneheptanoate, 10 parts of pyridine and 2 parts of acetic anhydride is kept at room temperature for about 16 hours, then is poured slowly into water. The resulting aqueous mixture is extracted with ether and the ether layer is separated, washed successively with dilute aqueous sodium bicarbonate and dilute aqueous sodium chloride, then dried over anhydrous sodium sulfate and concentrated to dryness under reduced pressure. The resulting residue is purified either by preparative thin layer chromatography using 20% ethyl acetate in benzene on silica gel or by dry chromatography on silica gel containing 8% water, also using 20% ethyl acetate in benzene. The resulting product, obtained as an oil, is methyl 3-acetoxy-5-oxo-2-styrylcyclopent-1-eneheptanoate. In chloroform, this compound exhibits infrared absorption maxima at about 5.75, 5.86, 6.15 and 8.02 microns. It exhibits also an ultraviolet absorption maximum at about 325 millimicrons with a molecular extinction coefficient of about 32,700. This compound is represented by the following structural formula

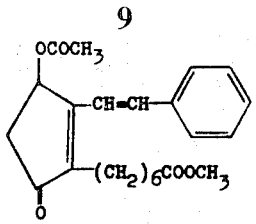

EXAMPLE 6

To a solution of 1.23 parts of methyl 3-acetoxy-5-oxo-2-styrylcyclopent-1-eneheptanoate in 20 parts of dioxane is added a solution of 0.81 part of osmium tetroxide in 3.85 parts of dioxane. The resulting reaction mixture is allowed to stand at room temperature for about 70 hours, at the end of which time the excess reagent is decomposed by the addition of hydrogen sulfide. The resulting solution is filtered through silica gel containing 8% of water and the adsorbent is washed with an ethyl acetate-methanol solution. The filtrate is concentrated and purified by dry column chromatography on silica gel containing 8% of water, using 50% ethyl acetate in benzene, thus affording, as an oil, methyl 3-acetoxy-5-oxo-2-($\alpha,\beta$-dihydroxyphenethyl)-cyclopent-1-eneheptanoate. This compound exhibits infrared absorption maxima, in chloroform, at about 2.78 and 5.78 microns and also an ultraviolet absorption maximum at about 234 millimicrons with a molecular extinction coefficient of about 10,900. It is characterized further by the following structural formula

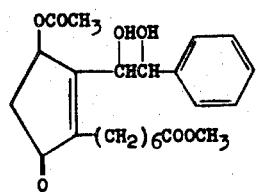

EXAMPLE 7

To a solution of 0.2 part of methyl 3-acetoxy5-oxo-2-($\alpha,\beta$-dihydroxyphenethyl)cyclopent-1-eneheptanoate in 8 parts of ethanol is added a solution of 0.12 part of sodium periodate in 2 parts of water. The resulting reaction mixture is allowed to stand at room temperature for about 45 minutes, then is diluted with water and extracted with ether. The ether layer is separated, washed with water, dried over anhydrous sodium sulfate and concentrated to dryness under reduced pressure. The resulting residue is heated under reduced pressure for about 10 minutes in order to remove benzaldehyde, thus affording the oily product, which is methyl 3-acetoxy2-formyl-5-oxocyclopent-1-eneheptanoate. It displays infrared absorption maxima, in chloroform, at about 5.78 and 5.92 microns.

EXAMPLE 8

To a suspension of 214 parts of triphenyl methyl phosphonium bromide with 1400 parts of ether, under nitrogen, is added, at 0°–5°, 190 parts by volume of a hexane solution containing 41.9 parts of n-butyl lithium. The resulting reaction mixture is allowed to warm to room temperature, then is stirred for about 1 hour and cooled to 0°–5°. A solution of 100 parts of n-hexanoyl chloride in 700 parts of ether is added under nitrogen and the resulting mixture is kept at room temperature for about 16 hours. At the end of that reaction period the ether solution is decanted and washed with dilute hydrobromic acid. The acidic washing is then shaken with the precipitate and the resulting solution is extracted with chloroform. The chloroform extract is washed successively with hydrobromic acid and water, dried over anhydrous sodium sulfate, concentrated to a small volume and diluted with hexane. The resulting crystals of starting material are removed by filtration and the filtrate is dissolved in chloroform, then washed successively with 20% aqueous potassium hydroxide, water, hydrobromic acid and water, dried over anhydrous sodium sulfate and concentrated to a small volume under reduced pressure. Dilution of the resulting solution with cyclohexane results in precipitation of the crystalline product, which is purified by recrystallization from aqueous ethanol to afford transparent needle-like crystals of triphenyl 2-oxoheptyl phosphonium bromide, melting at about 195°.

EXAMPLE 9

A solution of 0.19 part of triphenyl 2-oxoheptyl phosphonium bromide in 75 parts of chloroform is shaken with dilute aqueous potassium hydroxide, then washed with dilute aqueous sodium chloride, dried over anhydrous sodium sulfate, concentrated and dried at room temperature under reduced pressure. The resulting residue consisting of 0.16 part of hexanoylmethylene triphenyl phosphorane is combined with 0.13 part of methyl 3-acetoxy-2-formyl5-oxocyclopent-1-eneheptanoate and dissolved in 13.2 parts of benzene. The resulting reaction mixture is heated at the reflux temperature for about 24 hours, then is cooled and stripped of solvent under reduced pressure. The resulting residue is purified by dry column chromatography on silica gel containing 8% of water, using 20% ethyl acetate in benzene, to afford methyl 11-acetoxy-9,15-dioxoprosta-8(12),13-dienoate. This compound exhibits infrared absorption maxima, in chloroform, at about 5.78 and 6.28 microns and an ultraviolet absorption maximum at about 288.5 millimicrons with a molecular extinction coefficient of about 31,300.

EXAMPLE 10

A mixture consisting of 13 parts of 3-hydroxy-5-oxo-2-styrylcyclopent-1-eneheptanoic acid, 17.8 parts of sodium periodate, 55 parts of water, 160 parts of dioxane and 2 parts of 2% osmium tetroxide in dioxane solution is stirred under nitrogen at room temperature for about 4 hours. That reaction mixture is then extracted with ether and the ether layer is separated and extracted several times with 0.5% aqueous sodium chloride. The salt extracts are saturated with sodium chloride, then extracted with ether. The ether layer is separated, dried over anhydrous sodium sulfate, concentrated and dried under reduced pressure to afford 2-formyl-3-hydroxy-5-oxocyclopent-1-eneheptanoic acid, characterized by an ultraviolet absorption maximum at about 228 millimicrons with a molecular extinction coefficient of about 10,100.

EXAMPLE 11

To a solution of 10.2 parts of 2-formyl-3-hydroxy-5-oxocyclopent-1-eneheptanoic acid in 200 parts of dioxane is added 4 parts of triethylamine and the resulting mixture is stripped of excess triethylamine by distillation under reduced pressure. The resulting residue is dissolved in 210 parts of dioxane. To that dioxane solution is then added 15.3 parts of hexanoylmethylene triphenyl phosphorane, dissolved in 396 parts of benzene. The resulting reaction mixture is heated at the reflux temperature under nitrogen for about 18 hours, then is cooled, washed with aqueous oxalic acid and extracted with aqueous potassium bicarbonate. That alkaline extract is washed with ether, then acidified with oxalic acid and extracted with ether. The ether extract is washed with aqueous sodium chloride, dried over anhydrous sodium sulfate and concentrated to dryness under reduced pressure to afford the crude product, which is purified by dry column chromatography on silica gel containing 8% of water, using 4% methanol in benzene or by chromatography on silica gel and elution with 40% ethyl acetate in benzene, thus affording 11-hydroxy-9,15-dioxoprosta-8(12),13-dienoic acid, characterized by an ultraviolet absorption maximum at about 291 millimicrons with a molecular extinction coefficient of about 21,900.

EXAMPLE 12

To a solution of 0.25 part of lithium metal in 70 parts of liquid ammonia is added a solution of 1 part of 11-hydroxy-9,15-dioxoprosta-8(12),13-dienoic acid in 18 parts of tetrahydrofuran. The reaction mixture is stirred for about 10 minutes, at the end of which time 5 parts of solid ammonium chloride is added rapidly. The ammonia is evaporated under a stream of nitrogen and the resulting residue is cooled to 0°–5°, then diluted with ether. To the resulting suspension is added excess cold aqueous citric acid until the mixture is distinctly acidic. The resulting layers are separated and the aqueous layer is extracted with ether. The combined ether solutions are washed several times with aqueous sodium chloride, then dried over anhydrous sodium sulfate and concentrated to dryness under nitrogen to afford an orange oily residue. That oil is dissolved in 25% ethyl acetate in benzene solution and purified by dry column chromatography on silica gel containing 8% of water and 2% of glacial acetic acid, using ethyl acetate as the solvent, to afford a fraction which is 11-hydroxy-9,15-dioxoprost-8(12)-enoic acid, characterized by an ultraviolet absorption maximum at about 233 millimicrons with a molecular extinction coefficient of about 13,900.

EXAMPLE 13

To a solution of 12 parts of 11-hydroxy-9,15-dioxoprosta-8(12),13-dienoic acid in 28 parts of ethanol, cooled to 0°–5°, is added dropwise a solution of 3 parts of triethylamine in 275 parts of water. To that mixture is added dropwise with cooling and stirring a solution of 0.32 part of sodium borohydride in 32 parts of water. Stirring at approximately 10° is continued for about 25 minutes, at the end of which time the reaction mixture is poured carefully into excess aqueous citric acid. Extraction with ether affords an organic solution, which is washed with water, dried over anhydrous sodium sulfate and concentrated under reduced pressure to afford 11,15-dihydroxy-9-oxoprosta-8(12),13-dienoic acid. This mixture of epimeric 11-hydroxy compounds is separated by chromatography on silica gel. Elution with 30% ethyl acetate in chloroform affords epimer A, characterized by an ultraviolet absorption maximum at about 277 millimicrons with a molecular extinction coefficient of about 24,400. Further elution of the column with 50% ethyl acetate in chloroform yields epimer B, characterized by an ultraviolet absorption maximum at about 277.5 millimicrons with a molecular extinction coefficient of about 23,400.

EXAMPLE 14

A mixture of 13.5 parts of methyl 3-hydroxy5-oxo-2-styrylcyclopent-1-eneheptanoate, 17.8 parts of sodium periodate, 55 parts of water, 160 parts of dioxane and 2 parts by volume of a 2% osmium tetroxide in dioxane solution is stirred at room temperature under nitrogen for about 4 hours. The reaction mixture is extracted with ether and the ether solution is dried over anhydrous sodium sulfate, then concentrated to dryness under reduced pressure. The resulting residue is purified by dry column chromatography on silica gel containing 8% of water, using 50% ethyl acetate in benzene, thus affording methyl 2-formyl-3-hydroxy-5-oxocyclopent-1-eneheptanoate, characterized by an ultraviolet absorption maximum at about 228 millimicrons with a molecular extinction coefficient of about 10,200.

EXAMPLE 15

To a solution of 3.4 parts of methyl 3-hydroxy5-oxo-2-styrylcyclopent-1-eneheptanoate in 40 parts of dioxane is added successively 1.3 parts by volume of a 2% osmium tetroxide in dioxane solution and a solution of 4.28 parts of sodium periodate in 14 parts of water. The resulting reaction mixture is stirred at room temperature for about 3 hours, then is extracted with ether and the ether extract is poured through a column of anhydrous sodium sulfate, then concentrated to dryness under reduced pressure. The latter residue together with hexanoylmethylene triphenyl phosphorane, prepared from 4.1 parts of triphenyl methyl phosphonium chloride by the procedure described in Example 9, is dissolved in 200 parts of benzene and that reaction mixture is heated at the reflux temperature under nitrogen for about 20 hours. The solvent is removed by distillation under reduced pressure and the residual material is purified by dry column chromatography on silica gel containing 8% of water, using 50% ethyl acetate in benzene, thus affording methyl 11-hydroxy-9,15-dioxoprosta-8(12),13-dienoate, which compound exhibits an ultraviolet absorption maximum at about 291.5 millimicrons with a molecular extinction coefficient of about 24,600.

EXAMPLE 16

To a solution of 6.8 parts of methyl 3-hydroxy5-oxo-2-styrylcyclopent-1-eneheptanoate and 2 parts of pyridine in 80 parts of dioxane is added, at 0°–5°, a solution of 2.4 parts of chloroacetyl chloride in 20 parts of dioxane. The resulting reaction mixture is stirred at that temperature for about 30 minutes, then at room temperature for about 5 hours. At the end of that reaction period the mixture is poured carefully into ice water and the resulting aqueous mixture is extracted with ether. The ether solution is washed successively with dilute hydrochloric acid and dilute aqueous sodium bicarbonate, then dried over anhydrous sodium sulfate and stripped of solvent under reduced pressure. The resulting product is purified by dry column chromatography on silica gel containing 8% of water, using 18% ethyl acetate in benzene, to afford pure methyl 3-chloroacetoxy-5-oxo-2-styrylcyclopent-1-eneheptanoate. This compound is represented by the following structural formula

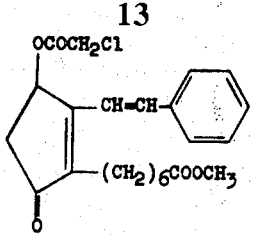
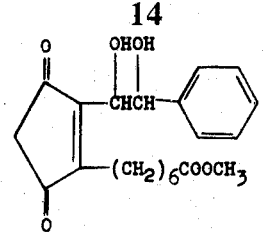

EXAMPLE 17

To a suspension of 1.3 parts of chromium trioxide with 15 parts of pyridine is added a solution of 1.5 parts of methyl 3-hydroxy-5-oxo-2-styrylcyclopent-1-eneheptanoate in 8 parts of pyridine and the resulting reaction mixture is stirred at room temperature for about 1 hour, then is allowed to stand at that temperature for about 16 hours. To the reaction mixture ice water is then added carefully and the resulting aqueous mixture is extracted with methylene chloride. The organic extract is washed successively with dilute hydrochloric acid and dilute aqueous sodium chloride, then dried over anhydrous sodium sulfate and stripped of solvent under reduced pressure. The resulting residue is purified by dry column chromatography on silica gel containing 8% of water followed by extraction of the column with 18% ethyl acetate in benzene. The resulting crystalline product is purified further by recrystallization from benzenecyclohexane to afford methyl 3,5-dioxo-2-styrylcyclopent-1-eneheptanoate, obtained as yellow needle-like crystals melting at about 62.5°. This compound displays ultraviolet absorption maxima at about 340.5 and 250.5 millimicrons with molecular extinction coefficients of 24,000 and 10,500, respectively. It is further characterized by the following structural formula

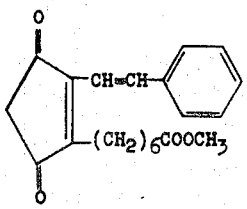

EXAMPLE 18

A mixture containing 1.7 parts of methyl 3,5-dioxo-2-styrylcyclopent-1-eneheptanoate, 1.44 parts of osmium tetroxide and 30 parts of dioxane is allowed to stand at room temperature for about 6 days. The reaction mixture which has solidified during that period is diluted with dioxane and hydrogen sulfide gas is bubbled into the resulting suspension. The inorganic insolubles are removed by filtration and the filtrate is concentrated to dryness under reduced pressure. Purification of the resulting residue by dry column chromatography, using a silica gel column containing 8% of water and 50% ethyl acetate in benzene as the solvent, affords methyl 3,5-dioxo-2-(α,β-dihydroxyphenethyl)cyclopent-1-eneheptanoate, which displays an ultraviolet absorption maximum at about 247.5 millimicrons with a molecular extinction coefficient of about 10,750. This compound is represented by the following structural formula

EXAMPLE 19

To a cold solution of 0.8 part of potassium hydroxide in 10 parts of water is added 2 parts of ethyl 3-oxooctanoate and that mixture is stirred at 0°–5° until homogeneous. The homogeneous mixture is kept at 0°–5° for about 72 hours, then is neutralized to pH 7 by the addition of concentrated aqueous citric acid. To that mixture is then added successively 2.5 parts by volume of 1 M citrate buffer of pH 4.8 and a solution of 2.5 parts of 2-formyl-3-hydroxy-5-oxocyclopent-1-eneheptanoic acid in 4.8 parts of methanol containing 2.5 parts of water. The pH is adjusted to 4.5–5.0 and the mixture is stirred for approximately 3 hours at about 35°, then is allowed to stand at room temperature for about 16 hours. The reaction mixture is extracted with ether and the ether layer is separated, dried over anhydrous sodium sulfate and stripped of solvent under reduced pressure to afford, as a pale yellow glass, 11,13-dihydroxy-9,15-dioxoprost-8(12)-enoic acid, which compound displays an ultraviolet absorption maximum at about 233 millimicrons with a molecular extinction coefficient of about 11,500.

EXAMPLE 20

A solution of 8.27 parts of 2-formyl-3-hydroxy-5-oxocyclopent-1-eneheptanoic acid in 150 parts by volume of 50% aqueous acetic acid is stirred at 0°–5° with 15 parts of zinc powder for about 2 hours. At the end of that time the mixture is filtered and the filtrate is diluted with approximately 200 parts by volume of saturated aqueous sodium chloride. Extraction of that mixture with ether affords an organic solution, which is washed with saturated aqueous sodium chloride, then dried over anhydrous sodium sulfate and stripped of solvent under reduced pressure. The resulting residue is combined with n-hexanoylmethylene triphenyl phosphorane, prepared from 27.2 parts of n-hexanoylmethyl triphenyl phosphonium chloride according to the procedure of Example 9, then is dissolved in a mixture of 100 parts of dioxane and 440 parts of benzene. The resulting mixture is heated under nitrogen at the reflux temperature for about 5½ hours, then is concentrated to dryness under reduced pressure. The resulting residue is extracted with ether and the ether extract is washed with cold hydrochloric acid, then with cold water and is finally extracted with cold aqueous potassium bicarbonate. The alkaline extract is acidified by the addition of citric acid and that acidic mixture is extracted with ether. The ether solution is washed with water, dried over anhydrous sodium sulfate and concentrated to dryness under reduced pressure to afford a mixture of 11α-hydroxy-9,15-dioxoprost-13-enoic acid and 11β-hydroxy-9,15-dioxoprost-13-enoic acid. Separation of those epimers is achieved by partition chromatography on silica gel, wherein the solvents are prepared by shaking together 500 parts by volume of hexane, 1,000 parts by volume of benzene, 500 parts by volume of methanol and 200 parts of water. The lower layer is used as the stationary phase and the upper layer as the eluant. Elution of the column affords 11β-hydroxy-9,15-dioxoprost-13-enoic acid, characterized by an ultraviolet absorption maximum at about 228.5 millimicrons with a molecular extinction coefficient of about 11,400, followed by 11α-hydroxy-9,15-dioxoprost-13-enoic acid, which exhibits an ultraviolet absorption maximum at about 228.5 millimicrons with a molecular extinction coefficient of about 10,700.

EXAMPLE 21

To a solution of 6.95 parts of hydroxylamine hydrochloride and 16.4 parts of sodium acetate dissolved in 80 parts by volume of 50% aqueous methanol is added a solution of 6.5 parts of 3-hydroxy-5-oxo-2-styrylcyclopent-1-eneheptanoic acid and 0.8 parts of sodium hydroxide in 30 parts by volume of 50% aqueous methanol. That mixture is allowed to stand for 48 hours. After that time, the reaction mixture is acidified with citric acid and filtered to yield crystals which, when recrystallized from 50 parts by volume of methanol, gives 3-hydroxy-5-hydroxyimino-2-styrylcyclopent-1-eneheptanoic acid. That compound melts at about 164° and displays, in methanol, an ultraviolet absorption spectrum with a peak at about 321 millimicrons with a molecular extinction coefficient of about 44,700. That compound is represented by the following structural formula

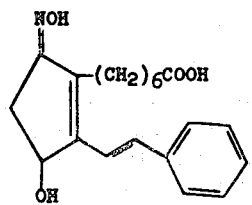

EXAMPLE 22

A solution of 6.618 parts of 3-hydroxy-5-oxo-2-styrylcyclopent-1-eneheptanoic acid in 196 parts of isopropanol is shaken in the presence of 1.0 part of 5% palladium-on-carbon catalyst under a hydrogen atmosphere, 10–49 p.s.i., at about 52°. The reaction is allowed to continue for 48 minutes after which time, the catalyst is removed by filtration and the filtrate is concentrated to dryness under reduced pressure. The residue remaining is chromatographed on silicic acid with the eluant being benzene with increasing amounts of ethyl acetate. The hydrogenation products are successively eluted in the following sequence:

2β-Phenethyl-5-oxo-1α-cyclopentaneheptanoic acid, a colorless oil, characterized by absorption in the ultraviolet spectrum in methanol, at about 247.5, 253.5, 258, 260.5 and 267.5 millimicrons with molecular extinction coefficients of about 190, 220, 250, 250 and 220 respectively and absorption in chloroform, in the infrared spectrum at about 1740, 1718, 1605 and 1500 reciprocal centimeters, and represented by the structural formula shown below

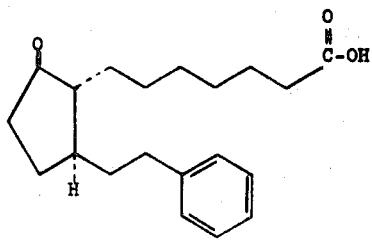

2β-Phenethyl-5-oxo-1α-cyclopent-3-eneheptanoic acid, a colorless oil, characterized in methanol, by an absorption band in the ultraviolet spectrum at about 218 millimicrons with a molecular extinction coefficient of about 12,600, maxima in the infrared spectrum in chloroform, at about 1710, 1607, 1591 and 1500 reciprocal centimeters, signals in the nuclear magnetic resonance spectrum at about δ 6.15, 7.03 and 7.63 and further characterized by the following structural formula

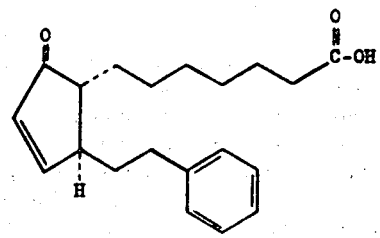

2-Phenethyl-5-oxocyclopent-1-eneheptanoic acid, melting at about 50° after recrystallization from cyclohexane, and characterized, in methanol, by an absorption band in the ultraviolet spectrum at about 239 millimicrons with a molecular extinction coefficient of about 14,000, signals in the nuclear magnetic resonance spectrum at about δ 2.78, and absorption peaks, in chloroform, in the infrared spectrum at about 1715, 1700, 1640, 1607, 1500 and structurally represented by the following formula

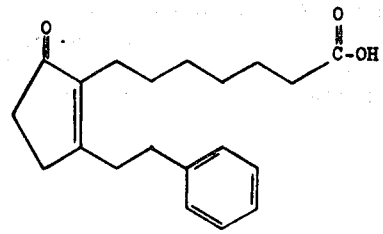

3β-Hydroxy-2β-phenethyl-5-oxo-1α-cyclopentaneheptanoic acid, a colorless glass, displaying signals in the nuclear magnetic resonance spectrum at about δ 4.47 and 7.27, absorption in the infrared spectrum, in chloroform, at about 3630, 1742, 1716, 1608 and 1500 reciprocal centimeters and represented by the following structural formula

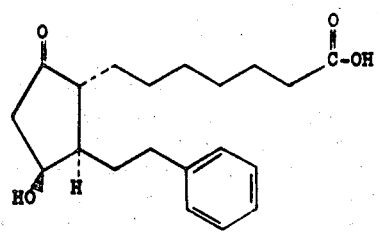

3-Hydroxy-2-phenethyl-5-oxocyclopentaneheptanoic acid, a colorless oil, characterized by nuclear magnetic absorption signals at about δ 4.45 and 7.25 and, in chloroform, by absorption maxima in the infrared spectrum at about 3620, 1740, 1715, 1605 and 1497 reciprocal centimeters. That compound is further represented by the following structural formula

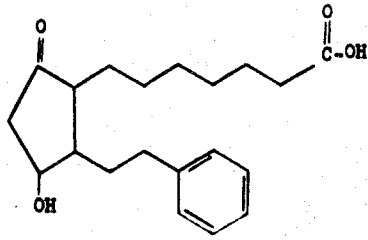

3α-Hydroxy-2β-phenethyl-5-oxo-1α-cyclopentaneheptanoic acid, a colorless glass, characterized by signals in the nuclear magnetic resonance spectrum at about δ 4.35 and 7.23, absorption, in chloroform, in the infrared spectrum at about 3620, 1740, 1710, 1604 and 1496 reciprocal centimeters, and further characterized by the following structural formula

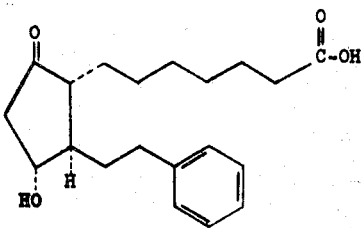

3-Hydroxy-2-phenethyl-5-oxocyclopent-1-eneheptanoic acid, a colorless glass, displaying, in methanol, an ultraviolet absorption band at about 235.5 millimicrons with a molecular extinction coefficient of about 10,200, nuclear magnetic resonance signals at about δ 4.80 and 7.23, and infrared absorption maxima, in chloroform, at about 3620, 1708, 1647, 1607 and 1500 reciprocal centimeters. That compound is structurally represented by the following formula

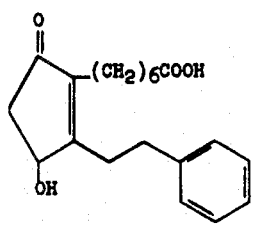

EXAMPLE 23

6 Parts of 3-hydroxy-5-oxo-2-styrylcyclopent-1-eneheptanoic acid is dissolved in 71 parts of ethanol and cooled to about 10° as 1.88 parts of triethylamine is added. The solution is stirred as 1.5 parts of sodium borohydride dissolved in 100 parts of water is added dropwise at 10°–15°. After stirring at about 15° for 4 hours, the mixture is acidified with dilute aqueous acetic acid and the oily precipitate is extracted with ethyl acetate. The organic solution is washed with dilute aqueous sodium chloride solution, dried over anhydrous sodium sulfate and concentrated to an orange oil. Then the oil is taken up in benzene and chromatographed on silicic acid as the column is eluted with benzene containing increasing amounts of ethyl acetate. A fraction eluted with 30% ethyl acetate is crystallized from ethyl acetate-hexane to give pale yellow crystals of 3-oxo-2-styrylcyclopent-1-eneheptanoic acid, melting at about 118°–120°. That compound displays, in chloroform, absorption peaks in the infrared spectrum at about 2940 and 1700 reciprocal centimeters and an absorption band, in methanol, in the ultraviolet spectrum at about 288 millimicrons with a molecular extinction coefficient of about 24,400. That compound is represented by the following structural formula

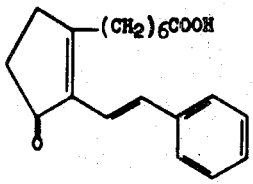

EXAMPLE 24

A cold solution of 1 part of 3-hydroxy-5-hydroxyimino-2-styrylcyclopent-1-eneheptanoic acid in 42.3 parts of dimethoxyethane is treated with a cold ethereal solution of diazomethane, prepared from 1.2 parts of N-nitrosomethylurea, 1.4 parts of potassium hydroxide and 2.5 parts of water. That mixture is allowed to react for 2 minutes, after which time, the cold excess diazomethane is decomposed by the careful addition of glacial acetic acid. The ethereal solution is washed with dilute aqueous sodium bicarbonate, then with water and dried over anhydrous sodium sulfate. The ether is removed and the crystalline residue is recrystallized from ethyl acetate-hexane to yield colorless crystals of methyl 3-hydroxy-5-hydroxyimino-2-styrylcyclopent-1-eneheptanoate. That compound melts at about 109°–110° and displays, in chloroform, absorption peaks in the infrared spectrum at about 3590 and 1735 reciprocal centimeters. It is further characterized by the following structural formula

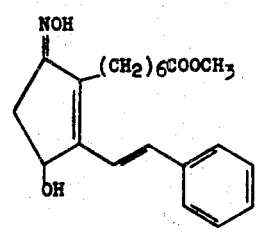

EXAMPLE 25

A solution of 2 parts of semicarbazide hydrochloride in 3 parts of water is combined with a solution of 2 parts of 3-hydroxy-5-oxo-2-styrylcyclopent-1-eneheptanoic acid dissolved in 2.95 parts of pyridine and 15.8 parts of ethanol. The resulting solution is allowed to stand for about 16 hours at room temperature. Then the crystalline precipitate is filtered, washed with an aqueous 80% ethanol solution and then with water. After drying, the material is recrystallized from boiling isopropanol to afford pale yellow crystals of 3-hydroxy-5-semicarbazono-2-styrylcyclopent-1-eneheptanoic acid, melting at about 208°–210°, and displaying, in potassium bromide, an infrared absorption spectrum with maxima at about 3480, 1720, 1693 and 1586 reciprocal centimeters. That compound further displays, in methanol, an absorption band in the ultraviolet spectrum at about 355 millimicrons with a molecular extinction coefficient of about 54,000 and is characterized by the following structural formula

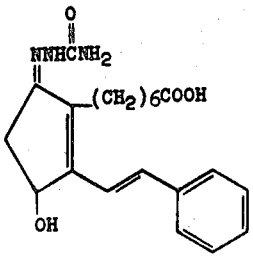

EXAMPLE 26

5 Parts of (−)-menthoxyacetic acid is dissolved in 8.79 parts of benzene and treated with 5.95 parts of oxalyl chloride. The resulting solution then is heated at about 60° for 2 hours and allowed to stand for 1 hour at room temperature. After that time, the solvent is removed under reduced pressure, and the remaining residue is dissolved in benzene and again concentrated to dryness. The crude (−)-menthoxyacetyl chloride thus obtained is dissolved in 8.79 parts of benzene and that solution added to a cold solution of 7.5 parts of 3-hydroxy-5-oxo-2-styrylcyclopent-1-eneheptanoic acid dissolved in 9.82 parts of pyridine. That mixture is allowed to stand for about 16 hours at room temperature, then poured into a cold solution of 50 parts of d-tartaric acid in 1,500 parts of water. The solution is extracted with ethyl acetate and the organic extracts are washed with water, dried over anhydrous sodium sulfate and concentrated to dryness. The oily residue which remains is dissolved in benzene and chromatographed on silicic acid to yield, after elution with 10% ethyl acetate-90% benzene, crude product. The pure material is obtained upon recrystallization from benzene-hexane to give 3-((−)-menthoxyacetoxy)-5-oxo-2-styrylcyclopent-1-eneheptanoic acid, melting at about 103°–104°, and displaying an optical rotation of about −42.1°. That compound is characterized by infrared absorption maxima, in chloroform, at about 1754, 1710, 1627 and 1124 reciprocal centimeters, an ultraviolet absorption band, in methanol, at about 326 millimicrons with a molecular extinction coefficient of about 37,000, and represented by the following structural formula

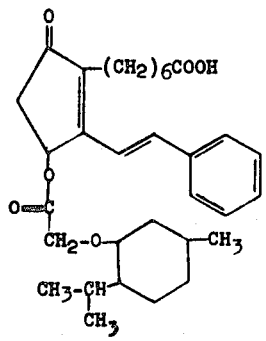

EXAMPLE 27

A mixture of 3.3 parts of (−)-O-methylmandelic acid, 44 parts of benzene, and 9.67 parts of oxalyl chloride is heated at 60°–70° for about 90 minutes. After removal of the solvent under reduced pressure, the remaining residue is dissolved in 26.4 parts of benzene and again concentrated to dryness. The crude (−)-O-methylmandelyl chloride thus obtained is taken up in 17.6 parts of benzene and added to a cold solution of 5.5 parts of 3-hydroxy-5-oxo-2-styrylcyclopent-1-eneheptanoic acid dissolved in 9.82 parts of dry pyridine. That mixture is allowed to stand for about 16 hours at room temperature and then it is poured into a cold solution containing 40 parts of d-tartaric acid in 1,350 parts of water. That mixture is extracted with ethyl acetate and the organic extracts are washed with water, dried over anhydrous sodium sulfate and concentrated to dryness. The oily residue which remains is dissolved in benzene and chromatographed on silicic acid. The fraction obtained upon elution with 15% ethyl acetate-85% benzene is recrystallized from benzene-hexane to give colorless crystals of 3β-((−)-O-methylmandeloxy)-5-oxo-2-styrylcyclopent-1-eneheptanoic acid, melting at about 122°–124° and displaying an optical rotation, in methanol, of about −22.2°. That compound is further characterized by absorption maxima, in chloroform, in the infrared spectrum at about 1,750, 1,710 and 1,630 reciprocal centimeters and an ultraviolet absorption band, in methanol, at about 326 millimicrons with a molecular extinction coefficient of about 36,000. It is represented by the following structural formula

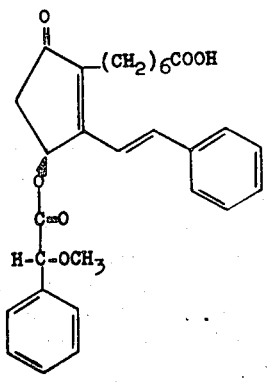

The latter fraction, obtained upon elution with 15% ethyl acetate, is recrystallized from benzene-hexane to give colorless needles of 3α-((−)-O-methylmandeloxy)-5-oxo-2-styrylcyclopent-1-eneheptanoic acid, melting at about 96°–98° and displaying, in methanol, an optical rotation of about −84.2°. That compound absorbs in the infrared spectrum, in chloroform, at about 1,750, 1,710 and 1630 reciprocal centimeters and has, in methanol, an absorption band in the ultraviolet spectrum at about 326 millimicrons with a molecular extinction coefficient of about 35,000. It is represented by the following structural formula

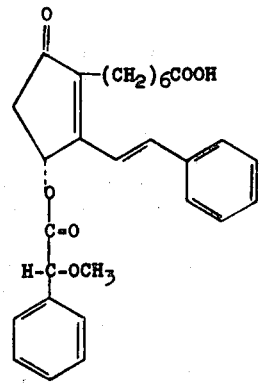

EXAMPLE 28

0.600 Part of 3β-((−)-O-methylmandeloxy)-5-oxo-2-styrylcyclopent-1-eneheptanoic acid is dissolved in 15.8 parts of methanol and treated with 20 parts by volume of a hydroxylamine solution prepared from 28 parts of hydroxylamine hydrochloride, 66 parts of sodium acetate and 320 parts of an aqueous 50% methanol solution. The resulting solution is allowed to stand at room temperature for 4 days. After that time the mixture is concentrated and then diluted with water. The precipitate which forms is washed with water, dried and recrystallized from ethyl acetate-hexane. The pure colorless 5-hydroxyimino-3β-((−)-O-methylmandeloxy)-2-styrylcyclopent-1-eneheptanoic acid which results melts at about 145°–147° and displays, in methanol, an optical rotation of about −22.8°. It is further characterized by an absorption band, in methanol, in the ultraviolet spectrum at about 322 millimicrons with a molecular extinction coefficient of about 42,500 and is represented by the following structural formula

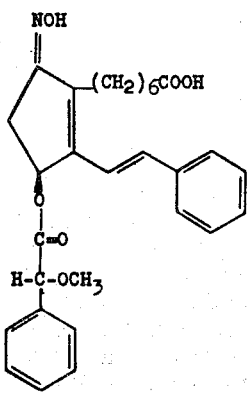

EXAMPLE 29

A solution of 0.300 part of 3β-((−)-O-methylmandeloxy)-5-oxo-2-styrylcyclopent-1-eneheptanoic acid in 2.66 parts of tetrahydrofuran is added to 30 parts by volume of a 1% aqueous potassium carbonate solution. That mixture then is allowed to stand at room temperature under a nitrogen atmosphere in subdued light for 3 days. The resulting solution is cooled in ice and acidified with dilute aqueous acetic acid. Then the product is isolated by filtration, taken up in ethyl acetate, washed with water, dried over anhydrous sodium sulfate, and dried under reduced pressure. The crude residue is dissolved in a small amount of 50% benzene-ethyl acetate and chromatographed on silicic acid suspended in 50% benzene-ethyl acetate. Elution with the same solvent yields the crude product which is recrystallized from benzene containing a small amount of ethyl acetate to give pure colorless crystals of (+)-3β-hydroxy-5-oxo-2-styrylcyclopent-1-eneheptanoic acid, melting at about 112°–114° and displaying, in methanol, an optical rotation of about +12.6°. That compound further displays an absorption band in the ultraviolet spectrum at about 326 millimicrons with a molecular extinction coefficient of about 35,600 and is represented by the following structural formula

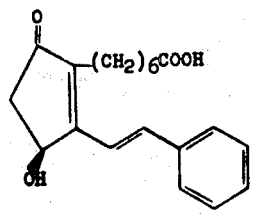

EXAMPLE 30

By substituting an equivalent quantity of 3α-((−)-O-methylmandeloxy-5-oxo-2-styrylcyclopent-1-eneheptanoic acid in the procedure of Example 29, there is obtained (−)-3α-hydroxy-5-oxo-2-styrylcyclopent-1-eneheptanoic acid, melting at about 112°–113° and displaying, in methanol, an optical rotation of about −16.5°. That compound is represented by the following structural formula

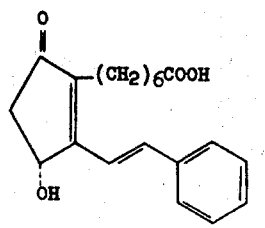

EXAMPLE 31

When an equivalent quantity of (+)-3β-hydroxy-5-oxo-2styrylcyclopent-1-eneheptanoic acid is substituted in the procedure of Example 10, there is produced (+)-2-formyl-3β-hydroxy-5-oxocyclopent-1-eneheptanoic acid.

EXAMPLE 32

Substitution of an equivalent quantity of (−)-3α-hydroxy-5-oxo-2-styrylcyclopent-1-eneheptanoic acid in the procedure of Example 10 and otherwise following the procedure of Example 10 yields (−)-2-formyl-3α-hydroxy-5-oxocyclopent-1-eneheptanoic acid.

EXAMPLE 33

When an equivalent quantity of propionic anhydride is substituted in the procedure of Example 5, there is produced methyl 3-propionoxy-5-oxo-2-styrylcyclopent-1-eneheptanoate.

EXAMPLE 34

Substitition of an equivalent quantity of diazoethane in the procedure of Example 4 yields ethyl 3-hydroxy-5-oxo-2-styrylcyclopent-1-eneheptanoate.

EXAMPLE 35

When an equivalent quantity of (30)-O-methylmandelic acid is substituted in the procedure of Example 27, there are produced 3β-((+)-O-methylmandeloxy)-5-oxo-2-styrylcyclopent-1-eneheptanoic acid, displaying an optical rotation in methanol of +84°, and 3α-((+)-O-methylmandeloxy)-5-oxo-2-styrylcyclopent-1-eneheptanoic acid, displaying an optical rotation in methanol of +20°.

These compounds are respectively characterized by the following structural formulas

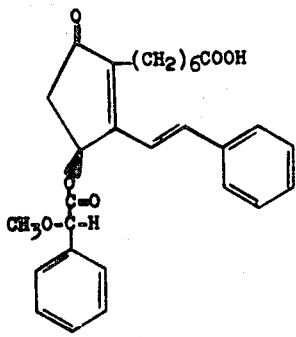

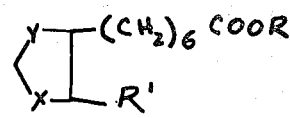

What is claimed is:
1. A compound of the formula

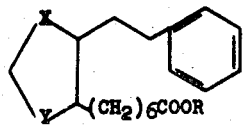

wherein R is hydrogen or a lower alkyl, R' is a, α,β-dihydroxyphenethyl, or phenethyl radical, Y is carbonyl, hydroxyiminomethylene, or semicarbazonomethylene radical, and X is a carbonyl radical or a radical of the formula

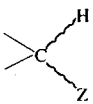

with Z being hydroxy, (−)-menthoxyacetoxy, (−)-O-methyl-mendeloxy, (+)-Omethylmandeloxy, (lower alkanoyl)oxy or chloro(lower alkanoyl)oxy and the wavy lines represent the α and β stereochemical configuration or the racemic mixture.

2. As in claim 1, a compound of the formula

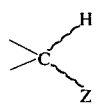

wherein R is selected from the group consisting of hydrogen and lower alkyl radicals, Y is selected from the group consisting of hydroxyiminomethylene, semicarbazonomethylene and carbonyl radicals and X is selected from the group consisting of carbonyl and radical of the formula with Z being hydroxy, (−)-menthoxyacetoxy, (−)-O-methylmandeloxy, (+)-O-methylmandeloxy, (lower alkanoyl)oxy and chloro(lower alkanoyl)oxy and the wavy lines representing the α and β stereochemical configuration or the racemic mixtures.

3. As in claim 1, the compound which is 2β-phenethyl-5-oxo-1α-cyclopentaneheptanoic acid.

4. As in claim 1, the compound which is 3β-hydroxy-2β-phenethyl-5-oxo-1α-cyclopentaneheptanoic acid.

5. As in claim 1, the compound which is 3-hydroxy-2-phenethyl-5-oxocyclopentaneheptanoic acid.

6. As in claim 1, the compound which is 3α-hydroxy-2β-phenethyl-5-oxo-1α-cyclopentaneheptanoic acid.

* * * * *